United States Patent
Dai et al.

(10) Patent No.: US 11,485,978 B2
(45) Date of Patent: Nov. 1, 2022

(54) DNA AND METHOD FOR PREPARING HETERODIMER SNAKE VENOM PROTEIN

(71) Applicant: Zhaoke Pharmaceutical (HEFEI) Company Limited, Anhui (CN)

(72) Inventors: Xiangrong Dai, Anhui (CN); Xiaoyi Li, Shatin NT (HK); Fang Qian, Anhui (CN)

(73) Assignee: Zhaoke Pharmaceutical (HEFEI) Company Limited, Anhui (CN)

( * ) Notice: Subject to any disclaimer, the term of this patent is extended or adjusted under 35 U.S.C. 154(b) by 553 days.

(21) Appl. No.: 16/341,343

(22) PCT Filed: Nov. 1, 2016

(86) PCT No.: PCT/CN2016/104175
§ 371 (c)(1),
(2) Date: Apr. 11, 2019

(87) PCT Pub. No.: WO2018/068347
PCT Pub. Date: Apr. 19, 2018

(65) Prior Publication Data
US 2020/0048644 A1    Feb. 13, 2020

(30) Foreign Application Priority Data
Oct. 14, 2016   (CN) .......................... 201610899516.3

(51) Int. Cl.
| | | |
|---|---|---|
| *C07K 14/46* | (2006.01) | |
| *C12N 15/81* | (2006.01) | |
| *A61P 7/02* | (2006.01) | |
| *C12N 1/16* | (2006.01) | |
| *A61K 38/00* | (2006.01) | |

(52) U.S. Cl.
CPC ............... *C12N 15/81* (2013.01); *A61P 7/02* (2018.01); *C07K 14/46* (2013.01); *C12N 1/16* (2013.01); *A61K 38/00* (2013.01); *C12N 2800/102* (2013.01)

(58) Field of Classification Search
None
See application file for complete search history.

(56) References Cited

U.S. PATENT DOCUMENTS

2020/0048644 A1*   2/2020   Dai ...................... C07K 14/46

FOREIGN PATENT DOCUMENTS

| CN | 101838323 A | 9/2010 |
|---|---|---|
| CN | 103263662 A | 8/2013 |
| CN | 103263663 A | 8/2013 |
| WO | WO2018068347 | 4/2018 |

OTHER PUBLICATIONS

Chen et al. (Acta Biochimica et Biophysica Sinica, Jan. 2000, vol. 32(6), pp. 653-656).*
Guo, Y. et al., "Balancing the expression and production of a Heterodimeric protein: recombatant Agkisacutacin as a novel antithrombotic drug candidate", Scientific Reports, Retrieved from the Internet http://www.nature.com/scientificreports, vol. 5:11730, (Nov. 2014).
Yu, H. et al., "Deinagkistrodon acutus clone 2100658 C-type lectin mRNA, complete cds", Genbank AY091759.1, (May 13, 2002).
Yu, H. et al., "Deinagkistrodon acutus antithrombin 1 B chain mRNA, complete cds", Genbank AF463521.1, (Jan. 21, 2002).
Yu, H. et al., "C-type lectin [Deinagkistrodon acutus]", Genbank AAM22787.1, (May 13, 2002).
Yu, H. et al., "antithrombin 1 B chain [Deinagkistrodon acutus]", Gembank AAL66390.1, (Jan. 21, 2002).

* cited by examiner

*Primary Examiner* — Hope A Robinson
(74) *Attorney, Agent, or Firm* — McHale & Slavin, P.A.

(57) ABSTRACT

Provided are recombinant plasmids containing the gene of the heterodimeric snake venom protein Agkisacutacin A chain and Agkisacutacin B chain, cell strains containing the recombinant plasmids, and a method for expressing the heterodimeric snake venom protein Agkisacutacin. The expression level of Agkisacutacin in the present method exceeds 10 mg/L, and the purity level can reach more than 95% by means of two steps of purification.

3 Claims, 3 Drawing Sheets

Specification includes a Sequence Listing.

DNA AND METHOD FOR PREPARING
HETERODIMER SNAKE VENOM PROTEIN

CROSS REFERENCE TO RELATED
APPLICATIONS

This application is a national stage filing in accordance with 35 U.S.C. § 371 of PCT/CN2016/104175, filed Nov. 1, 2016, which claims the benefit of the priority of Chinese Patent Application No. 201610899516.3, entitled "METHOD FOR PREPARING HETERODIMERIC SNAKE VENOM PROTEIN", filed on Oct. 14, 2016. The contents of each are incorporated herein by reference.

TECHNICAL FIELD

The present disclosure relates to a preparation method of recombinant protein, in particular to a preparation method of a recombinant protein drug heterodimer snake venom.

BACKGROUND

Cardio-cerebrovascular diseases, especially thrombus-induced cerebral and myocardial infarction seriously threat human health and affect the quality of life of patients. These diseases are now the third leading cause of death in the world, not only bringing great threat to the patient's life during acute attack, but also leading to huge expenditure of material resources and financial resources because of the easily occurring bad recovery. Therefore, it is urgent to find new safe and effective drugs for these diseases. The effect of snake venom on blood coagulation system has been paid more and more attention, and some ingredients of snake venom are effective drugs to treat these diseases.

Antiplatelet thrombolysin from Agkistrodon acutus venom is a C-type lectin like protein, which was found on the basis of separation, purification and activity study on snake venom protein of the life science school, Chinese University of Science and Technology (CUST) for many years, which is named Agkisacutacin, and Chinese name antiplatelet thrombolysin. Agkisacutacin is a heterodimer, and the apparent molecular weights of the two subunits are very close, both around 14-15 kDa. The molecular weight of Agkisacucetin was accurately determined by MALDI-TOF MS to be 30 kDa. The sequence and crystal structure of Agkisacucetin were finally obtained by N-terminal sequence determination of amino acid, LC-MS, crystal structure of Agkisacucetin protein, etc. Agkisacutacin has the activity of inhibiting platelet aggregation, and previous studies have laid an important foundation for the development of this protein into a new class of antithrombotic drugs.

At present, the main source of Agkisacutacin is the extraction of natural snake venom. The source of natural snake venom is limited, the purification process is complex and the yield is low, which limits the scientific research and clinical application of Agkisacutacin as an antithrombotic drug.

SUMMARY OF THE INVENTION

One of the purposes of the present disclosure is to provide a recombinant plasmid pPIC9K-A, as shown in FIG. 1, the sequence of Agkisacutacin A chain gene was shown in SEQ ID NO:1; a plasmid pUCZ-B, as shown FIG. 2, the sequence of Agkisacutacin B chain gene is shown in SEQ ID NO:2.

The present disclosure also provides a transformant, comprising one of the recombinant plasmid pPIC9K-A, plasmid pUCZ-B or their combination.

The present disclosure also provides a transformant, which expresses recombinant heterodimer snake venom protein, wherein the heterodimer snake venom protein consists of two peptide chains of A chain and B chain, the A chain amino acid sequence is shown in SEQ ID NO:3, and the B chain amino acid sequence is shown in SEQ ID NO:4.

Preferably, the transformant is a cell strain *Pichia* strain.

In particular, in the examples of the present disclosure, cell strains with the accession number CCTCC No. M2016358 are, provided, which is classified as *Pichia pastoris* GS115. It expresses recombinant heterodimer snake venom protein, consisting of two peptide chains named A chain and B chain, wherein the A chain amino acid sequence is shown as SEQ ID NO:3 and the B chain amino acid sequence is shown as SEQ ID NO:4.

The present disclosure also provides use of the plasmids and the transformants in the preparation of a medicament for treatment of thrombosis.

The present disclosure also provides a method of mass expression of a recombinant heterodimer snake venom protein, comprising the steps of:

Batch phase: introducing a secondary seed of the transformant according to any one of claims 4 to 6 into a basic salt medium with pH 4.0 to 6.0, adding glycerin to 4% to amplify bacteria and when the dissolved oxygen (DO) content rises sharply, the batch phase ends;

Conversion phase: continuously supplying 50% glycerol solution containing 10-15 ml/L PTM1, with a flow rate of 10-15 ml/h/L, which process lasting until to a wet weight of 190-200 g/L;

Methanol induction phase: stopping adding glycerin when the wet weight reaching 190-200 g/L, adding methanol solution containing 12 ml/L PTM1 at a constant restrictive methanol flow rate, with a stirring speed of 800-1200 rpm, and a total fermentation time of 70-90 hours, and wet weight reaching 400-600/L;

Protein purification: after the fermentation, adjusting the fermentation broth pH to 8.0, conducting a high speed centrifugation, and purification by passing through a column to obtain the recombinant heterodimer snake venom protein.

Preferably, the whole process has a temperature of 28-34° C.

The present disclosure also provides a recombinant protein prepared by the described method.

The present disclosure adopts the whole gene synthesis method, obtains its coding gene from the known protein sequence and structure form of Agkisacutacin. It was found that the methanol-utilizing *Pichia pastoris* was an ideal Agkisacutacin expression system, and a large amount Agkisacutacin of high purity was obtained by recombinant expression. The experiment verified the recombinant Agkisacutacin expressed by yeast is a heterodimer protein and has biological activities.

At the first time the present disclosure adopts *Pasteurus pastoris* to express Agkisacutacin, and pilot scale study on fermentation process was performed. Under the condition of high density fermentation, the amount of expression was more than 10 mg/L; after three steps of purification, the purity was over 95%. In addition, the present disclosure also provides a simple but robust fermentation process for the production of Agkisacutacin.

Biomaterial Deposition

The cell strain of *Pichia pastoris* GS115 was deposited under the Budapest Treaty under the accession number CCTCC No. M2016358 at the Chinese Typical Culture Conservation Center, Wuhan University, No. 299 Bayi Road, Wuyi District, Wuhan City, Hubei Province, China, on Jun. 30, 2016.

SPECIFIC MODE OF IMPLEMENTATION

Figure 1:
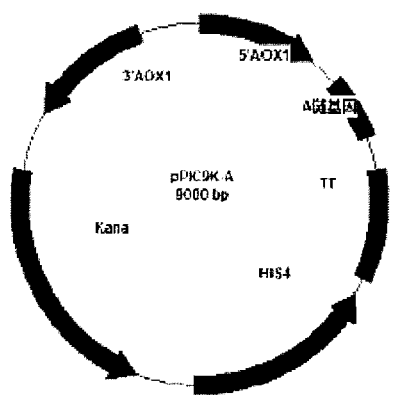
FIG. 1 shows the structure of Agkisacutacin A chain expression vector.

The present disclosure discloses a preparation method of a heterodimer snake venom protein. Those skilled in the art can practise it by reference to this disclosure with proper improvement to the process parameters. In particular, it should be stated that all similar replacements and changes are obvious to those skilled in the art and are considered to be included in the present invention. The product and method of the present disclosure has been described through embodiments. It is apparent that those skilled in the art can modify or appropriately modify and combine the methods and applications described herein within the contents, spirit and scope of the present disclosure, so as to realize and apply the technology of the present disclosure.

The present disclosure will be further elaborated in combination with examples below:

1. Experimental Materials 1.1 Strain and Plasmid

*P. pastoris* strain GS115, pPIC9K vector purchased from Invitrogen company, PUCZ vector (Zeocin resistant) was constructed in our laboratory.

1.2 Reagents

Yeast nitrogen base (YNB) purchased from BD Company; RPMI-1640 medium purchased from Hyclone Company; Fetal bovine senim purchased from Gibco Company; Yeast extract and Trypton purchased from OXOID Company; BCA protein detection kit purchased from Pierce Company; d-Sorbitolam d-biotin, plasmid extraction kit, PCR product recovery kit, gel recovery kit, DNA polymerase, T4 DNA linking enzyme, restriction endonuclease, protein marker and PAGE related reagents purchased from Shanghai Bioengineering; PHA and Endoglycosidase H (Endo H) purchased from Sigma-Aldrich Company; EZ-ECL chemiluminescence test kit purchased from Biological Industries Company; other chemical reagents purchased from the Chinese Medicines Group. Si-containing defoamer purchased from Jiangsu Saiouxinyue Defoamer Agent Co., Ltd.; and Anti-Agkisacutacin antibody 1B9 derived from Zhaoke Pharmaceutical Company Ltd.

1.3 Instruments

Electronic analytical balance and pH meter purchased from Mettler Toledo Co., Ltd; vortex oscillometer oscillator purchased from Scientific Industries Company; electrophoresis instrument, vertical electrophoretic tank, horizontal electrophoretic tank, gel imaging system purchased from Tianeng Company; semi-dry film conversion instrument, electric rotary instrument purchased from Bio-Rad Company; chemiluminescence detector purchased from UVITEC Company; high pressure sterilizer purchased from Hirayama Company; table refrigeration centrifuge (Centrifuge 5810R, Centrifuge 5415R) purchased from Eppendorf Co., Ltd; super clean workbench, rocker, constant temperature incubator purchased from Shanghai Zhicheng Co., Ltd.; PCR instrument purchased from Germany Biometra Company; enzyme labeling instrument (BLX-800) purchased from Bio-Tek Company; micro liquid remover purchased from Gilson Company of France; cell incubator purchased from Themo Company. AKTA explorer Labscale TFF System and Pellicon XL (10 kD) purchased from Millipore company; BioFlo®115 Benchtop Fermentor purchased from New Brunswick Scientific company; large sterilizer, Flex Stand system and 0.45 µm microfiltration cartridge purchased from GE healthcare; LTQ linear IT MS purchased from Thermo; and Ettan™ MDLC HPLC system purchased from GE healthcare.

1.4. Primer
1. AgkiA-Fw-Xho1:
TCTCTCGAGAAAAGAGATGTCGATTGTCTCCCTGGTTGGTC

2. AgkiA-Rv-Not1-ng:
ATATGCGGCCGCTTATGGCGGGGACTTGCAGACGAAAG

3. AgkiB-Fw-EcoR1:
CTGAATTCGGTTTCTGTTGTCCCTTGCGTTGTTCG

4. AgkiB-Rv-Not1-ng:
ATATGCGGCCGCTTATAGCTTGAACTTGCAGACGAAATAG

2. Experimental Method 2.1 Construction of Agkisacutacin A Chain Expression Vector I. Amplification of A Chain Target Gene with EcoR1 and Not1 Restriction Enzyme Cutting Sites The whole gene synthesis A chain DNA sequence was amplified by PCR under the guidance of primer AgkiA-Fw-Xho1 and AgkiA-Rv-Not1-ng. The PCR reaction conditions were as follows: First 94° C. for 2 minutes, then 94° C. for 30 seconds, 55° C. for 40 seconds, 72° C. for 30 seconds, a total of 32 cycles; finally at 72° C. for 10 minutes. After the reaction was finished, the PCR product was detected by 1% agarose gel electrophoresis, and a band of about 396 bp was obtained, which was consistent with the expected results. PCR product recovery kit was used to recover the target band.

II. Construction of *Pichia pastoris* Expression Vector with Recombinant Agkisacutacin A Chain The PCR products obtained from the above step were subjected to double enzyme digestion with restriction endonuclease EcoR1 and Not1, then the restriction fragment was linked to the plasmid pPIC9K subjected to the same double enzyme digestion by T4 DNA ligase. The linking product was transformed into *Escherichia coli* DH5α competent cells, and positive recombination was screened. Plasmids were extracted and identified by enzyme digestion, the identified positive clones were named pPIC9K-A, and sent to Shanghai Bioengineering for sequencing. The sequencing results showed that the DNA sequence between recognition sites EcoR1 and Not1 inserted into pPIC9K was in line with the expected results.

2.2 Construction of Agkisacutacin B Chain Expression Vector

I. Amplification of B Chain Target Gene with EcoR1 and Not1 Restriction Enzyme Cutting Sites The whole gene synthesis B chain DNA sequence was amplified by PCR under the guidance of primer AgkiB-Fw-EcoR1 and AgkiB-Rv-Not1-ng. The PCR reaction conditions were as follows: First 94° C. for 2 minutes, then 94° C. for 30 seconds, 55° C. for 40 seconds, 72° C. for 30 seconds, a total of 32 cycles, finally at 72° C. for 10 minutes. After the reaction was finished, the PCR product was detected by 1% agarose gel electrophoresis, and a band of about 381 bp was obtained, which was consistent with the expected results. PCR product recovery kit was used to recover the target band.

II. Construction of *Pichia pastoris* Expression Vector with Recombinant Agkisacutacin B Chain The PCR products obtained from the above step were subjected to double enzyme digestion with restriction endonuclease EcoR1 and Not1, then the restriction fragment was linked to the plasmid pPIC9K subjected to the same double enzyme digestion by T4 DNA ligase. The linking product was transformed into *Escherichia coli* DH5α competent cells, and positive recombination was screened. Plasmids were extracted and identified by enzyme digestion. The identified positive clones were named pPIC9K-B, and sent to Shanghai Bioengineering for sequencing. The sequencing results were completely in line with the expected results. The cloned plasmid was subjected to double enzyme digestion by BamH1 and Not1, and the small fragment was recovered. The recovered small fragment was linked to the plasmid pUCZ subjected to the same double enzyme digestion with T4 DNA ligase. The linking product was transformed into *Escherichia coli* DH5α competent cells, and positive recombination was screened. Plasmids were extracted and identified by enzyme digestion. The identified positive clones were named pUCZ-B, and sent to Shanghai Bioengineering for sequencing. The sequencing results were completely in line with the expected results.

2.3 Screening of Recombinant Agkisacutacin Expression Clones

The *Pichia pastoris* strain GS was streaked on YPD plates. After two days, the growing monoclone was picked out and cultured in YPD liquid medium. Two days later, the yeast grew to milky white, and this first species was introduced into YPD liquid medium, which was a secondary species. This secondary species was used to prepare yeast competent cells, which was electrotransformed into pPIC9K-A plasmid which had been linearized with Sal1 enzyme. MD plate was coated. After 48 to 72 hours, the monoclone grown on the plate were picked out and cultured in MGY liquid medium. After two days, the culture was centrifuged at 1500 g, the supernatant was discarded, and BMMY medium with pH 5.0 was added thereto and induced for 72 hours. During the process, 100% methanol was replenished every 24 hours to maintain methanol concentration in BMMY medium at 0.5%. After the end of induction, centrifuged at 12000 g, the supernatant was collected, and the expression of A chain protein was detected by SDS-PAGE, and the monoclone expression of A chain was screened out.

The GS115 monoclone expressing the A chain protein was streaked on the MD plate. After two days, the grown monoclone was picked out and cultured in MGY liquid medium. Two days later, the yeast grew to milky white, and this first species was introduced into YPD liquid medium, which was a secondary species. This secondary species was used to prepare yeast competent cells, which was electrotransformed into pUCZ-B plasmid which had been linearized with Spe1 enzyme. MD plate was coated with antibiotic Zeocin. After 48 to 72 hours, the monoclone grown on the plate were was picked out and cultured in MGY liquid medium supplemented with antibiotic Zeocin. After two days, the culture was centrifuged at 1500 g, the supernatant was discarded, and the BMMY medium with pH 5.0 was added thereto and induced for 72 hours. During the process, 100% methanol was replenished every 24 hours to maintain methanol concentration in BMMY medium at 0.5%. After the end of induction, centrifuged at 12000 g. the supernatant was collected. The expression of double chain protein was detected by Western Blot using monoclone antibody against Agkisacutacin. Monoclone *Pichia pastoris* GS115 expressing double strand was screened out, which was deposited on Jun. 30, 2016 at the Chinese Typical Culture Conservation Center, with the access number CCTCC No. M2016358, and was named as *Pichia pastoris* GS115.

2.4 Fermentation Expression of Recombinant Agkisacutacin (1) First species: Inoculated from frozen working strain bank to 4 ml MGY medium (MGY+Z) added with Zeocin, cultured at 30° C., 250 rpm for 36-48 h to $OD_{600}$=2-6, which was the fermentative first species;

(2) Secondary species: 1 ml of first species was inoculated into 200 ml BMGY with pH 5.0, cultured at 30° C. and 250 rpm for 12-18 h to $OD_{600}$=2-6, which was a fermentative secondary species.

(3) Fermentation preparation: fermentation tank was assembled and related reagents were prepared, sterilized and so on;

(4) Batch phase: The secondary species were inoculated into a 14 L fermentor containing 4 L basic salt medium of pH5.0. Basic salt medium containing 4% glycerol (pH 5.0) was used to amplify the bacteria in the batch phase wherein the culture temperature was 30° C. When DO rose sharply, the batch phase ended.

(5) Conversion period: When DO began to rise rapidly, it meant that glycerol in the original medium depleted, requiring constant supplementation of 50% glycerol solution containing 12 ml/L PTM1, the flow rate was 12 ml/h/L. This process lasted 4 hours to wet weight near 190 g/L;

(6) Methanol induction phase: When the wet weight reached near 190 g/L, the glycerine flow was stopped, and the dissolved oxygen rapidly increased, then a methanol solution containing 12 ml/L PTM1 was added at restricted flow of methanol at constant flow rate. The temperature was controlled at 30° C., the stirring rate was about 1000 rpm, the total fermentation time was about 80 hours, and the wet weight was about 500 g/L.

2.5 Purification of Recombinant Agkisacutacin (1) Solid-liquid separation: after fermentation, the fermentation broth pH was slowly adjusted to 8.0 with NaOH, centrifugation at 10000 g was performed for 20 min, and supernatuant was collected;

(2) Sample clarification: Flex Stand system 0.22 μm filter was used to clarify;

(3) Protein capture: recombinant Agkisacutacin in the fermentation broth was captured by Ion exchange column. The fermentation broth was dialysis and desalted by Flexstand ultrafiltration/filtration system. After desalting, the samples passed through the CM FF column, and 30% buffer B was used to elute the samples;

(4) Fine purification: some samples of the 30% elution were further purified by Q HP, eluted by gradient. The samples of different peaks were successively collected and the purity of the recombinant Agkisacutacin was detected by SDS-PAGE.

(5) Storage: stored with PBS frozen protein.

2.6 Activity Detection of Recombinant Agkisacutacin (1) Naturally extracted Agkisacutacin can bind to the GP1b site, and the binding ability of recombinant Agkisacutacin and recombinant GPIb was tested.

(2) Naturally extracted Agkisacutacin can inhibit platelet agglutination, and the inhibition of platelet agglutination by recombinant Agkisacutacin was studied.

Figure 2:
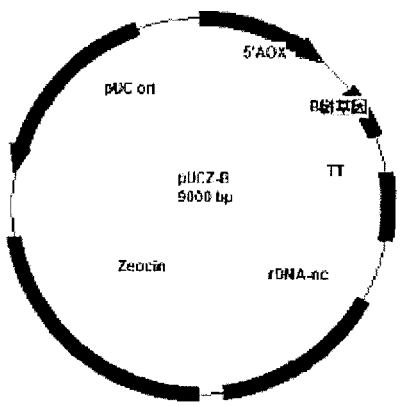
FIG. 2 shows the structure of Agkisacutacin B chain expression vector.

3 Experimental Results 3.1 the Construction of Agkisacutacin Expression Vector is Shown in FIG. 1 and FIG. 2.

The A chain of Agkisacutacin has a full length of 132 amino acids. The coding sequence of A chain was linked to the 3' terminal of α-Factor signal peptide of *Pichia pastoris*, and cloned into pPIC9K yeast expression vector. In this way, AOX I promoter was induced by methanol, so as to drive its downstream protein expression.

The B chain of Agkisacutacin has a full length of 127 amino acids. The coding sequence of B chain was linked to the 3' terminal of α-factor signal peptide of *Pichia pastoris*, and cloned into pUCZ yeast expression vector. In this way, AOX I promoter was induced by methanol, so as to drive its downstream protein expression.

3.2 Screening of Agkisacutacin Expression Strains

Figure 3:
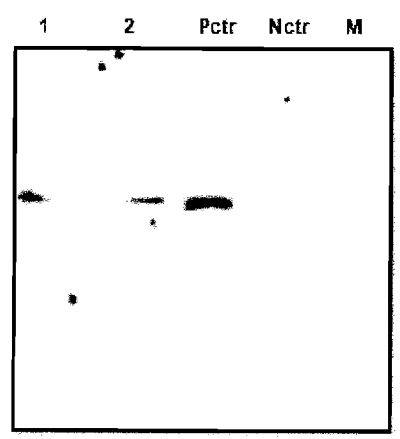
FIG. 3 shows the results of Western Blot detection of Agkisacutacin expression strain.

After multiple screenings, the clone of expressing Agkisacutacin was obtained. The Western Blot results are shown in FIG. 3.

Figure 4:
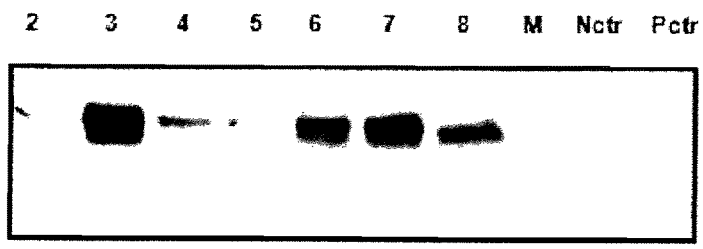
FIG. 4 shows the results of Western Blot detection of high expression strain of Agkisacutacin.

No. 1 clones was screened again, and seven expression clones were obtained. Western Blotting was used to detect the expression of Agkisacutacin in these clones, showing that all effectively expressed recombinant Agkisacutacin, as shown in FIG. 4.

3.3 Fermentation Expression of Recombinant Agkisacutacin in Pilot Scale

Figure 5:
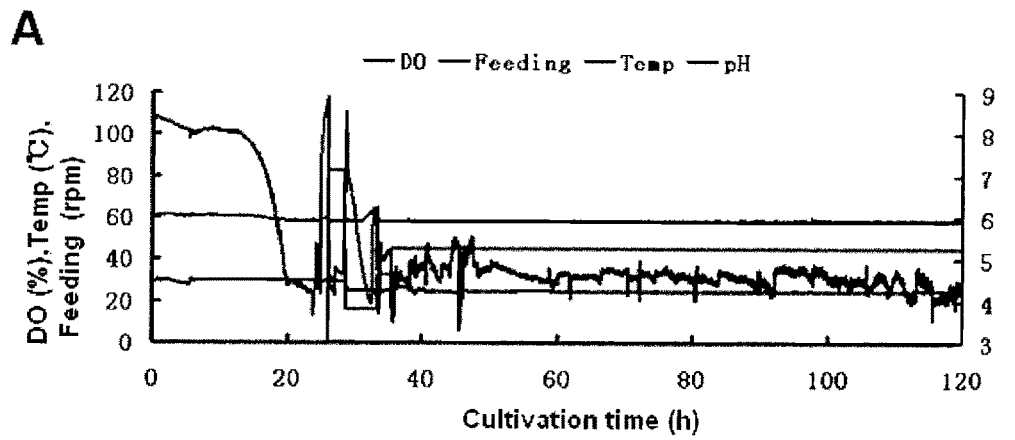
FIG. 5 shows the fermentation expression time curve of the pilot scale of recombinant Agkisacutacin.
Figure 6:
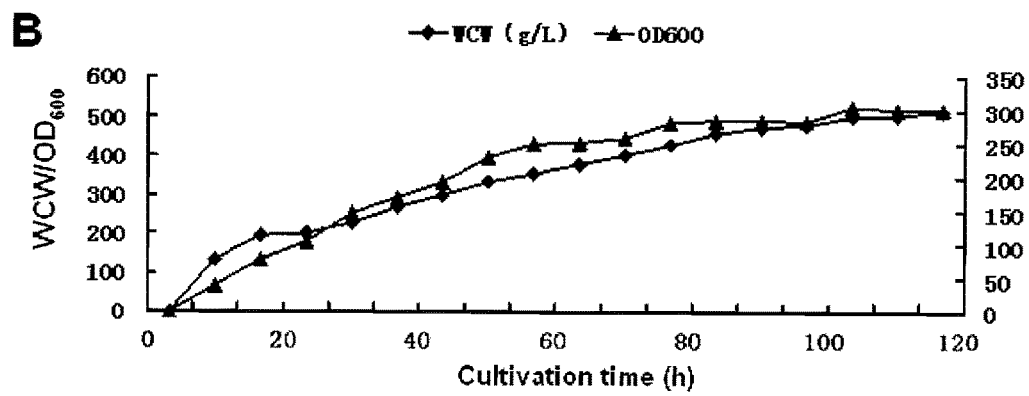
FIG. 6 shows the expression of double strand, A chain and B chain in the pilot scale of recombinant Agkisacutacin.

Methanol was added at restricted constant flow rate to perform fed-batch cultivation of the expression bacteria. At first, basic salt medium containing 4% glycerol (pH 5.0) was used to amplify the bacteria at 30° C. in the batch stage. When DO rose sharply, the batch phase ended, and the wet weight of the bacteria reached 134.7 g/L. Then was the conversion period, that is, the glycerol flow period, after about 4 hours of growth, the wet weight of the bacteria increased further to 193.6 g/L. At this time, the flow of glycerol was stopped, and the respiration activity of bacteria decreased and DO increased rapidly. Then methanol induction was performed, the respiration activity of the bacteria recovered, and the DO began to decrease gradually. In the methanol induction stage, because the bacteria have a phase of adaptation to methanol (2-4 hours), it is necessary to gradually increase the concentration of methanol during this period to avoid the toxicity of excessive accumulation of methanol to the bacteria. The whole fermentation process was very stable and the parameters were stable within the set ranges. At the end of fermentation, $OD_{600}$ exceeded 300, and the wet weight of bacteria reached 511.5 g/L. The results showed that the death rate of bacteria remained at a low level during the whole fermentation process, and methanol concentration was also stabilized at very low levels, maintaining the restricted growth of the bacteria, as seen in FIG. 5 and FIG. 6. Although the wet weight of the bacteria continuously increased during the induction, the expression of protein substantively reached balance after 80 hours of culture (or 60 hours of induction), and no longer accumulated. Therefore, it was more suitable to end fermentation at this time.

3.4 Purification and Identification of Agkisacutacin

After fermentation, pH of fermentation broth was adjusted to 8.0, after high-speed centrifugation and filtration and clarification via Flexstand 0.22 um, BCA was used to determine the total protein content in fermentation broth which was 1.6 g/L. The concentration of rAgkisacutacin was estimated by SDS-PAGE to be more than 100 mg/L. Because there was no ELISA kit for rAgkisacutacin detection in our Engineering center, so accurate quantification was not available.

Figure 7:
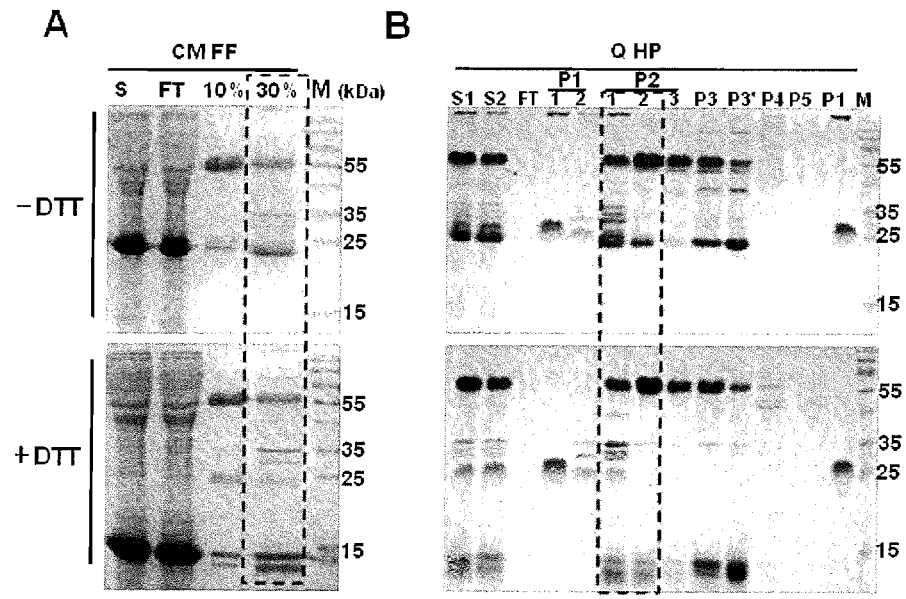
FIG. 7 shows the identification of protein Agkisacutacin.

Because rAgkisacutacin does not carry any tag, and we do not have a rAgkisacutacin antibody affinity column in our Engineering center, so we tried to use an ion exchange column to capture the rAgkisacutacin in the fermentation broth. By using Flexstand ultrafiltration/filtration system, the fermentation broth was dialyzed and desalted, and the desalted samples flowed through the CM FF column, and the samples were eluted with 10% and 30% buffer B (the purification conditions had been preliminarily explored by using a small ion exchange column of 1 ml in the early stage). It can be known from the test results that rAgkisacutacin was mainly present in the 30% elution (The presence of rAgkisacutacin in the sample can be determined by whether there are two closely connected bands of 15 kDa in the SDS-PAGE of DTT under the condition of reduction, and the protein purity can be analyzed by SDS-PAGE under non-reductive conditions). 10% elution also contained a small amount of rAgkisacutacin, and the content of A chain was higher than that of B chain, therefore, there should be a small amount of AA homologue dimer in 10% elution (FIG. 7A). Some samples of 30% elution were further purified by Q HP, and there were five peaks in gradient elution, wherein two peaks were continuously collected with 2-3 tubes (P1 and P2). By observing the two bands at the 15 kDa position in SDS-PAGE under the condition of reduction, it was found that rAgkisacutacin was mainly present in P2 peak, especially in P2-2 sample with the least impurity. The content of A chain in P3 peak was higher than that in B chain, therefore, there would be AA homologous dimer pollution. P1, P4, and P5 did not contain A or B chain (FIG. 7B).

Figure 8:
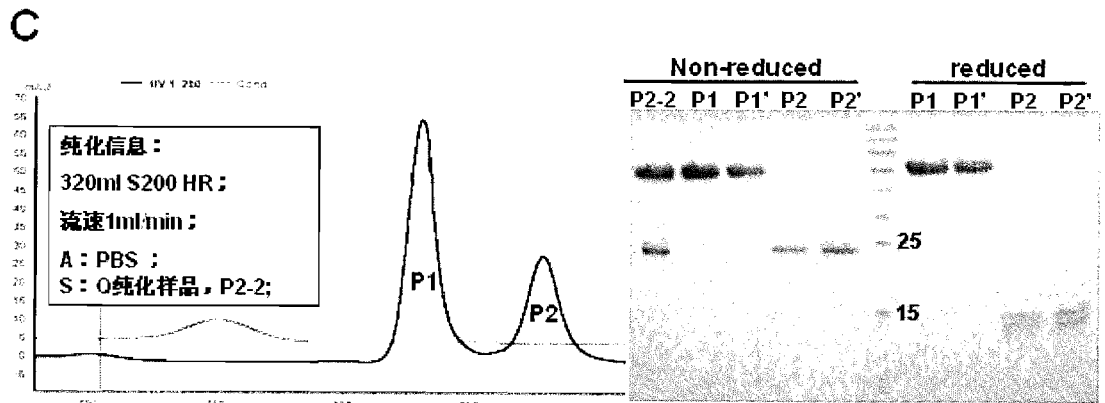
FIG. 8 shows the purification of protein Agkisacutacin.
Figure 9:
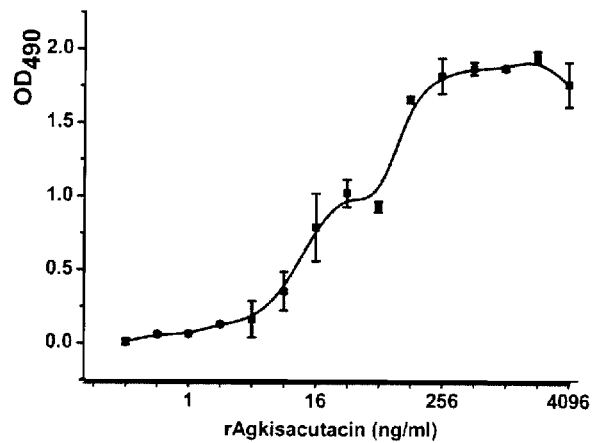
FIG. 9 shows the results of GP1b binding activity test of recombinant Agkisacutacin.

Since the P2-2 sample mainly contained two bands, and the locations thereof were quite different, so molecular sieve was used to purify. As expected, these two bands were well separated. It was confirmed via detection that the P2 in molecular sieve was the target protein rAgkisacutacin. Under the condition of non-reduction, there was a uniform band, and under the condition of reduction, there were two bands with basically the same content (see FIG. 8, P1' and P2' denote the peaks of P1 and P2 respectively). At present, the purity of P2 and P2' in these molecular sieves has not been identified, visual measurement shows that is should achieve a purity of 90%. By preliminary estimation, about 10 mg of purified samples can be obtained from 1 L fermentation broth.

3.5 Determination of Agkisacutacin Activity

GPIb binding activity and antiplatelet agglutination activity of purified product were tested. The results of GPIb binding activity showed that, recombinant Agkisacutacin can combine well with recombinant GPIb, and the relative affinity constant was estimated to be $10^{-7}$M (FIG. 9). The antiplatelet agglutination activity was detected by the Zhaoke Pharmaceutical company, and the experimental results showed that when the amount of protein reached 2 ug, platelet aggregation could be inhibited by 100% in the detection system; when the amount of protein was 1 ug, there was no inhibitory activity. All these experiments show qualitatively that, recombinant Agkisacutacin from yeast has biological activity and physiological function.

The above is only preferred embodiments of the present disclosure, it should be noted that a number of improvements and modifications may also be made by those skilled in the art without departing from the principle of the present disclosure, which should also be regarded fallen within the scope of protection of the present invention.

The invention claimed is:

1. A transformant with the accession number of CCTCC No. M2016358 comprising Plasmid pPIC9K-A, Plasmid pUCZ-B, and a gene of Agkisacutacin A chain of SEQ ID NO:1, and a gene of Agkisacutacin B chain of SEQ ID NO:2.

2. A method to produce a recombinant heterodimer snake venom protein, comprising the steps of:
   Batch phase: introduce a secondary seed of the transformant of claim 1 into a basic salt medium with pH 4.0 to 6.0, add glycerin to 4% to amplify the transformant and end the batch phase when the dissolved oxygen (DO) content rises sharply;
   Conversion phase: continuously supply a 50% glycerol solution containing 10-15 ml/L PTM1, with a flow rate of 10-15 ml/h/L, until a wet weight of 190-200 g/L is achieved;
   Methanol induction phase: stop adding glycerin when the wet weight reaches 190-200 g/L, add a methanol solution containing 12 ml/L PTM1 at a constant restrictive methanol flow rate, with a stirring speed of 800-1200 rpm, and a total fermentation time of 70-90 hours, until the wet weight reaches 400-600 g/L; and
   Protein purification: after the fermentation, adjust the pH of the fermentation broth to 8.0, conduct a high speed centrifugation, and conduct a purification by passing the precipitate through a column to produce the recombinant heterodimer snake venom protein.

3. The method of claim 2, wherein temperature of all steps is controlled at 28-34° C.

* * * * *

SEQUENCE LISTING

```
<160> NUMBER OF SEQ ID NOS: 4

<210> SEQ ID NO 1
<211> LENGTH: 508
<212> TYPE: DNA
<213> ORGANISM: artificial sequence
<220> FEATURE:
<223> OTHER INFORMATION: Recombinant plasmid

<400> SEQUENCE: 1
cmtcdsatgg ggcgattcat cttcgtgagc ttcggcttgc tggtcgtgtt cctctccctg      60
agtggaactg gagctgatgt cgattgtctc cctggttggt ctgcctatga tcagtcttgc     120
taccgggtct tcaaactcct caagacctgg gatgatgcag agaagttctg cacggagcgg     180
ccgaaaggcg ggcatctggt ctctatcgaa agcgcgggag agagagactt tgtggcccag     240
ctggtctctg agaacaaaca gacggacaat gtctggcttg gactgaagat tcaaagcaaa     300
ggacagcaat gcagcacaga gtggaccgat ggctccagcg tcagttatga gaatttttct     360
gaataccaat ccaaaaagtg ttttgtgctg gaaaaaaaca cagggtttcg cacatggctc     420
aatcttaatt gtggaagtga atatgctttc gtctgcaagt ccccgccata gtgttaagat     480
gcagctgagt gaagtctgga gaagcaag                                        508

<210> SEQ ID NO 2
<211> LENGTH: 487
<212> TYPE: DNA
<213> ORGANISM: artificial sequence
<220> FEATURE:
<223> OTHER INFORMATION: Recombinant plasmid

<400> SEQUENCE: 2
atggggcgat tcatcttcgt gagcttcggc ttgctggttg tgttcctttc cctaagggga      60
actggagctg gtttctgttg tcccttgcgt tggtcctcct atgaagggca ttgctacctg     120
gtcgtcaaag aaaagaagac ctgggatgat gcagagaaat tctgcacaga acagcgcaaa     180
ggcggccatc tggtctccgt tcacagcagg gaagaagcag attttttggt acacctcgcc     240
tacccaattt tggatctcag tttgatctgg atgggactga gcaacatgtg gaacgactgc     300
aagcgagagt ggagtgatgg caccaagctt gacttcaaat cctgggcaaa aacatctgat     360
tgtctcatcg gcaagacaga tggtgataac caatggttaa atatggactg cagcaagaaa     420
cactatttcg tctgcaagtt caagctatag tctgaagatg cagctgagtg aagtctggag     480
aagcaag                                                               487

<210> SEQ ID NO 3
<211> LENGTH: 130
<212> TYPE: PRT
<213> ORGANISM: artificial sequence
<220> FEATURE:
<223> OTHER INFORMATION: Recombinant heterodimer

<400> SEQUENCE: 3

Asp Val Asp Cys Leu Pro Gly Trp Ser Ala Tyr Asp Gln Ser Cys Tyr
1               5                   10                  15

Arg Val Phe Lys Leu Leu Lys Thr Trp Asp Asp Ala Glu Lys Phe Cys
            20                  25                  30
```

-continued

```
Thr Glu Arg Pro Lys Gly Gly His Leu Val Ser Ile Glu Ser Ala Gly
        35                  40                  45

Glu Arg Asp Phe Val Ala Gln Leu Val Ser Glu Asn Lys Gln Thr Asp
 50                  55                  60

Asn Val Trp Leu Gly Leu Lys Ile Gln Ser Lys Gly Gln Gln Cys Ser
 65                  70                  75                  80

Thr Glu Trp Thr Asp Gly Ser Ser Val Ser Tyr Glu Asn Phe Ser Glu
                 85                  90                  95

Tyr Gln Ser Lys Lys Cys Phe Val Glu Lys Asn Thr Gly Phe Arg Thr
                100                 105                 110

Trp Leu Asn Leu Asn Cys Gly Ser Glu Tyr Ala Phe Val Cys Lys Ser
            115                 120                 125

Pro Pro
    130

<210> SEQ ID NO 4
<211> LENGTH: 125
<212> TYPE: PRT
<213> ORGANISM: artificial sequence
<220> FEATURE:
<223> OTHER INFORMATION: Recombinant heterodimer

<400> SEQUENCE: 4

Gly Phe Cys Cys Pro Leu Arg Trp Ser Ser Tyr Glu Gly His Cys Tyr
 1               5                  10                  15

Leu Val Val Lys Glu Lys Lys Thr Trp Asp Asp Ala Glu Lys Phe Cys
                20                  25                  30

Thr Glu Gln Arg Lys Gly Gly His Leu Val Ser Val His Ser Arg Glu
            35                  40                  45

Glu Ala Asp Phe Leu Val His Leu Ala Tyr Pro Ile Leu Asp Leu Ser
 50                  55                  60

Leu Ile Trp Met Gly Leu Ser Asn Met Trp Asn Asp Cys Lys Arg Glu
 65                  70                  75                  80

Trp Ser Asp Gly Thr Lys Leu Asp Phe Lys Ala Trp Ala Lys Thr Ser
                 85                  90                  95

Asp Cys Leu Ile Gly Lys Thr Asp Asp Asn Gln Trp Leu Asn Met Asp
                100                 105                 110

Cys Ser Lys Lys His Tyr Phe Val Cys Lys Phe Lys Leu
            115                 120                 125
```